(12) United States Patent
Patel

(10) Patent No.: US 10,448,865 B1
(45) Date of Patent: Oct. 22, 2019

(54) TOOTH MOBILITY MEASURING APPARATUS

(71) Applicant: Tim J Patel, Walnut Creek, CA (US)

(72) Inventor: Tim J Patel, Walnut Creek, CA (US)

( * ) Notice: Subject to any disclaimer, the term of this patent is extended or adjusted under 35 U.S.C. 154(b) by 679 days.

(21) Appl. No.: 14/848,002

(22) Filed: Sep. 8, 2015

(51) Int. Cl.
*A61B 5/11* (2006.01)
*A61B 5/00* (2006.01)

(52) U.S. Cl.
CPC .......... *A61B 5/1111* (2013.01); *A61B 5/0053* (2013.01); *A61B 5/682* (2013.01); *A61B 5/6838* (2013.01); *A61B 5/74* (2013.01); *A61B 2562/0261* (2013.01)

(58) Field of Classification Search
CPC ......... A61B 5/1111; A61B 5/682; A61B 9/00; A61C 19/04; G01B 3/002
See application file for complete search history.

(56) References Cited

U.S. PATENT DOCUMENTS 5,483,751 A * 1/1996 Kodato ................. G01B 3/002
33/794
5,803,730 A * 9/1998 Khademazad ........ A61B 5/1111
356/614

FOREIGN PATENT DOCUMENTS

DE             4003947 A1 *  8/1991  ........... A61B 5/1111

* cited by examiner

*Primary Examiner* — Patrick Fernandes
(74) *Attorney, Agent, or Firm* — Theodore J. Bielen, Jr.

(57) ABSTRACT

A manually operable apparatus for measuring tooth mobility utilizing an alveolar ridge clamped and a tooth clamp. A positioning rod of the alveolar clamp serves as an anchor. A metering rod of the tooth indicates tooth mobility to a gage when force is applied to the same.

6 Claims, 3 Drawing Sheets

TOOTH MOBILITY MEASURING APPARATUS

BACKGROUND OF THE INVENTION

The present invention relates to a novel and useful apparatus for measuring the mobility of a tooth.

Periodontal disease is characterized by a human developing swelling of the gums which is associated with bleeding upon provocation. In addition, the gum tissue (gingiva) and jaw (alveolar) bone loss also occurs. The primary etiology of periodontal disease is linked to plaque and tartar (calculus). The end stage of periodontal disease is marked by tooth loss, bone loss, and attachment loss.

During the development of periodontal disease, teeth develop an abnormal mobility. In other words, teeth become loose relative to attachment to the jaw. In the past, the degree of looseness has been measured without any accurate instrumental devices. The standard procedure for measuring mobility consists of placement of two ends of a dental instrument on a tooth and the application of an alternating back and forth force on such instruments to initiate movement of the tooth. The degree of mobility from this method is then "eyeballed" by the dental practitioner who the guesses as to the degree of mobility.

Teeth found in the human jaw have a natural or physiological mobility of 0-0.25 mm. Thus, such level of natural of mobility does not indicate a disease state or a state related to a trauma. Teeth possess a natural mobility because teeth are not firmly attached directly to the jawbone, but are separated by a periodontal ligament. The periodontal ligament generally functions as a natural shock absorber.

Thus, mobility beyond 0.25 mm, indicates a trauma condition or existence of periodontal disease. A classification system, known as the Miller Scale, sorts tooth mobility into three classes. Class 1 is defined as a tooth movement or a mobility of up to 1 mm. Class 2 is defined as a horizontal movement between 1 mm and 2 mm. Finally, class 3 mobility takes place when tooth movement lies between 2 mm and 3 mm, with depressible vertical mobility.

In the past, the need to measure tooth mobility has been recognized. For example, Russian Patent 219653701, Japanese Patent 3552894 B2, Japanese Patent 3625035 B2, and Japanese Patent 4272917 B2 show devices and methods that use probes or piston that apply a force to the tooth and gages that detect the physical movement of such piston or probe.

U.S. Pat. Nos. 4,192,321, 4,470,810, and 5,680,874 show apparatuses for measuring tooth mobility in which a movable probe, positioned against a tooth, generates an electrical signal that is interpreted as an indication of movement of the tooth.

U.S. Pat. No. 5,803,730, Japanese Patent 3620979 B2, and Japanese Patent 2008048992 A show devices for measuring tooth mobility in which the movement of a contacting member on the tooth is transferred into an optical signal indicating the distance of movement of the tooth.

Russian Patent 2068242 C1 and Russian Patent 2223063 C1 show devices for indicating tooth mobility utilizing a clamping sleeve or clamp in combination with a rod to indicate tooth movement on the application of a force on the rod.

An apparatus for measuring tooth mobility and detecting the possibility of periodontal disease in a simple mechanical fashion would be a notable advance in the dental arts.

SUMMARY OF THE INVENTION

In accordance with the present invention a novel and useful apparatus for measuring tooth mobility is herein provided.

Apparatus of the present application is formed with a base member. Also, a first clamp is utilized to grip the alveolar ridge having an overlying tissue. The first clamp includes a positioning rod connected to the base member. The first rod fixes the distance between the first clamp and the base member.

A second clamp is also employed in the present invention and is adapted to grip the tooth. The second clamp includes a metering rod connected to the second clamp and extended to the base member for sliding engagement with the same. The metering rod also includes an end portion for manual engagement apart from the base member. The first and second clamps may comprise spring loaded clamps. Also, the sliding engagement between the metering rod and the base member may include a provision of a guide found on the base member.

A gage is also found in the apparatus of the present application and is mounted to the metering rod and the base member. The gage is utilized for measuring movement of the metering rod upon the application of a force on the metering rod end portion. The gage specifically includes a scale fixed to the base member. A rotatable indicator element is rotatably mounted to the scale through a pivot. The metering rod, that is moveable through the guide relative to the base member, includes an arm. A linkage connects the arm to the indicator element to allow rotation of the indicator element relative to scale.

In certain cases, a strain gage may be interposed the end portion of the metering rod and the end portion of the metering rod to indicate the degree of force applied to the metering rod, and, consequently, to the tooth being measured, that is held by the clamp at an end portion of the metering rod.

The scale of the gage may take the form of an open frame having a leg with first and second sides, opposite to one another. Each side being marked with indicia alignable with the indicator element showing movement of the metering rod relative to the base member.

It may be apparent that a novel and useful apparatus for measuring tooth mobility has been hereinabove described.

It is therefore an object of the present invention to provide an apparatus for metering the mobility of a tooth that is simple and reliable in use.

Another object of the present invention is to provide an apparatus for metering the mobility of a tooth that manually operated and is substantially mechanical in its characteristic.

A further object of the present invention is to provide an apparatus for metering the mobility of a tooth that accurately measures the mobility of a tooth according to accepted values of the Miller Scale.

Another object of the present invention is to provide an apparatus for metering the mobility of a tooth that includes the combination of clamps, one adapted to grip the alveolar ridge and the other to grip the tooth.

A further object of the present invention is to provide a device for metering the mobility of a tooth that may be easily used on teeth found in the upper and lower jaws of a patient.

The invention possesses other objects and advantages especially as concerns particular characteristics and features thereof which will become apparent as the specification continues.

Figure 1:
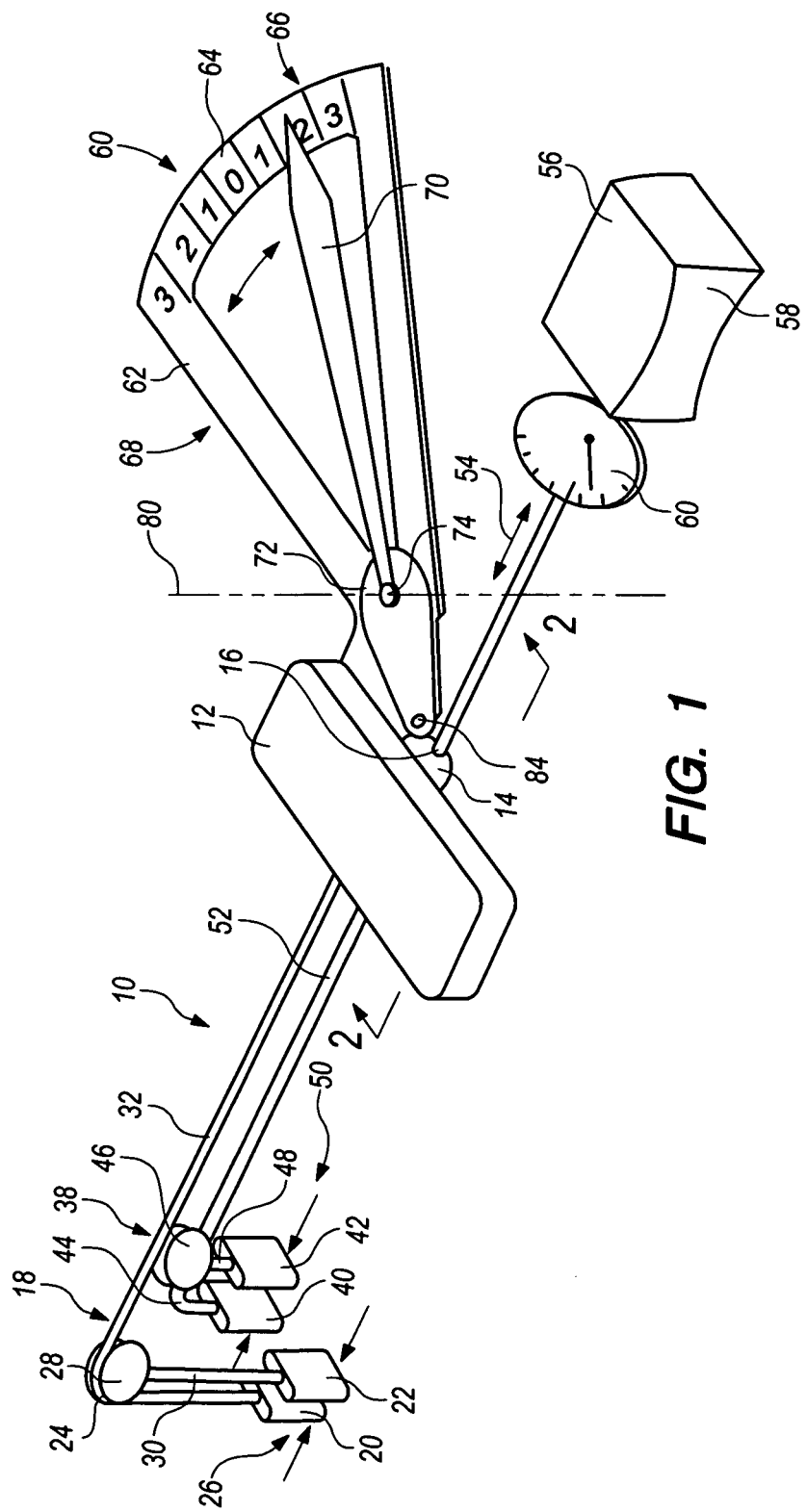
FIG. 1 is a top right perspective view of the device of the present invention.

For a better understanding of the invention reference is made to the following detailed description of the preferred embodiments of the invention which should be taken in conjunction with the above described drawings.

DETAILED DESCRIPTION OF THE PREFERRED EMBODIMENTS OF THE INVENTION

Various aspects of the present invention will evolve from the following detailed description of the preferred embodiments thereof which should be referenced to the prior delineated drawings.

The device of the present application, as a whole, is depicted in the drawings by reference character 10. Apparatus 10 includes as one of its elements, a base member 12 generally in the shape of a rectangular solid. Base member 12 may be formed of any rigid or semi-rigid material. Base member 12 includes a flange 14 having a passageway 16 therethrough, FIG. 1.

Figure 2:
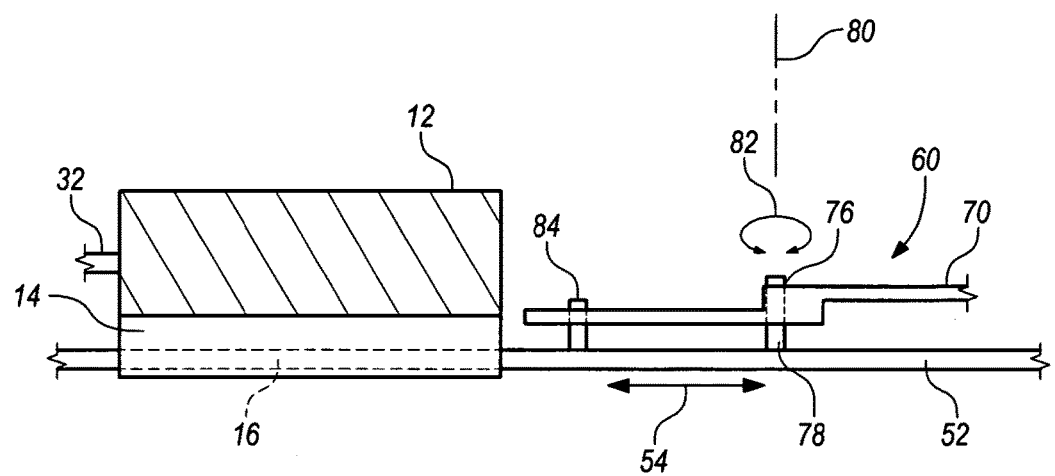
FIG. 2 is a sectional view taken along 2-2 of FIG. 1.

With further reference to FIGS. 1 and 2, apparatus 10 is also provided with a first clamp 18. First clamp 18 includes a pair of pads 20 and 22. Clamp 18 is spring loaded by dint of the resilience of arm 24. That is to say, pads 20 and 22 are spring biased toward one another and separable upon the application of a force opposite to one other. Directional arrows 26 indicate the biasing of pads 20 and 22 towards one another. Case 28 serves as a support for spring arm 24 and support arm 30 for pad 22. Positioning rod 32 connects to base member 12 and to case 28 of clamp 18. In certain cases, rod 32 may be unitary with spring arm 24 connecting to pad 20. In any case, positioning rod 32 fixes the distance of clamp pad 20 and 22 from base member 12, generally serving as an anchor. First clamp 18 is adapted to grip alveolar ridge 34 having overlying tissue adjacent teeth 36, shown on FIG. 3, the details of which will be discussed as the specification continues.

Referring again to FIGS. 1 and 2, it should be observed that a second clamp 38 is depicted therein. Second clamp 38 is formed with opposing pads 40 and 42 and is spring loaded by dint of spring arm 44. Again, case 46 supports spring arm 44 and support arm 48 for pad 42, directional arrow 50 show the biasing of pads 40 and 42 toward one another. In this regard, pads 40 and 42 operate in substantially the same manner as pads 20 and 22 of first clamp 18. Clamp 38 is also provided with a metering rod 52 which connects to case 46 of second clamp 38 and extends to and slidingly engages base member 12. Such sliding engagement takes places through passageway or guide 16, FIGS. 1 and 2. Directional arrow 54 indicates the back and forth movement of metering rod 52 during the use of apparatus 10, which will be discussed hereinafter. An end portion 56 is found at the terminus of metering rod 52 and takes the form of a grip or handle 58. An optional strain gage 60, of conventional configuration, may be interposed by grip 58 and rod 52 to indicate the amount of force along metering rod 52 exerted by the user of device 10 in a push-pull connection.

A gage 60 is also formed as part of device 10. Gage 60 includes an open frame 62 having a leg 64 marked with indicia 66. It should be noted that a reverse side of leg 64 depicted in FIG. 1 also includes identical indicia as that shown. Thus, open frame 62 and leg 64 having indicia 66 comprises a scale 68. Scale 68 is fixed to base member 12. Scale 68 also includes a moveable, rotatable indicator element or pointer 70. Indicator element 70 is fixed to a plate 72. Plate 72 and indicator element 70 rotate about a pivot 74 formed by a pivot pin 78 extending from open frame 62, FIG. 2. Thus, indicator element 70 and plate 72 rotate about an axis 80 according to directional arrow 82, FIGS. 1 and 2. Gage 62 also includes an arm 84 fixed to and extending from metering rod 52, which moves back and forth according to directional arrow 54, commensurate with the force exerted by the user on metering rod 52 via grip 58. Needless to say, the back and forth movement of arm 84 results from the rotation of indicator element 70 and plate 72 about pivot pin 76 at pivot 74. Further, it should be realized that arm 84 extending from metering rod 52 fits into an opening in plate 72 and slightly rotates relative to plate 72 with the back and forth movement of arm 84 and metering rod 52.

Figure 3:
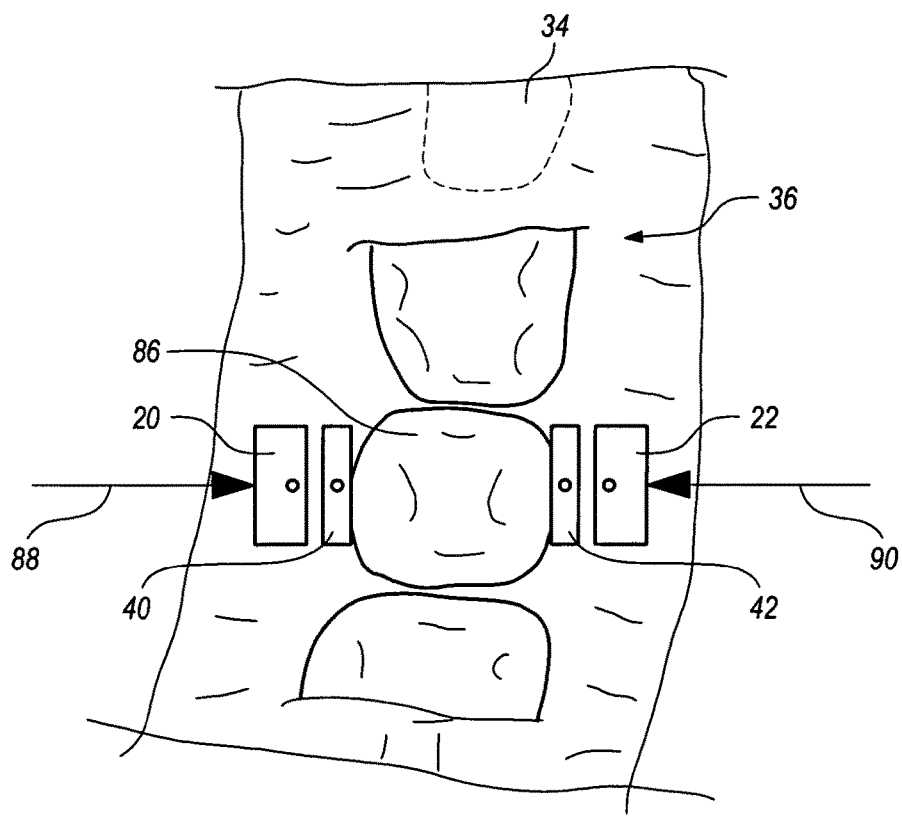
FIG. 3 is a top plan view of a partial jaw having a tooth being measured by the apparatus of the present invention, which is indicated solely by the clamps engaging the tooth and the alveolar ridge.
Figure 4:
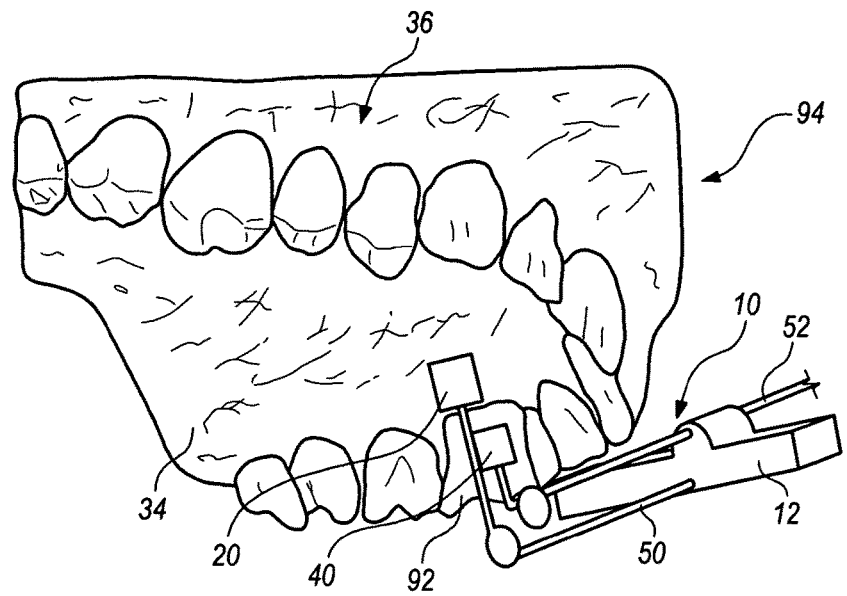
FIG. 4 is a perspective view of the apparatus of the present invention being employed to measure tooth mobility on the upper jaw of a patient.
Figure 5:
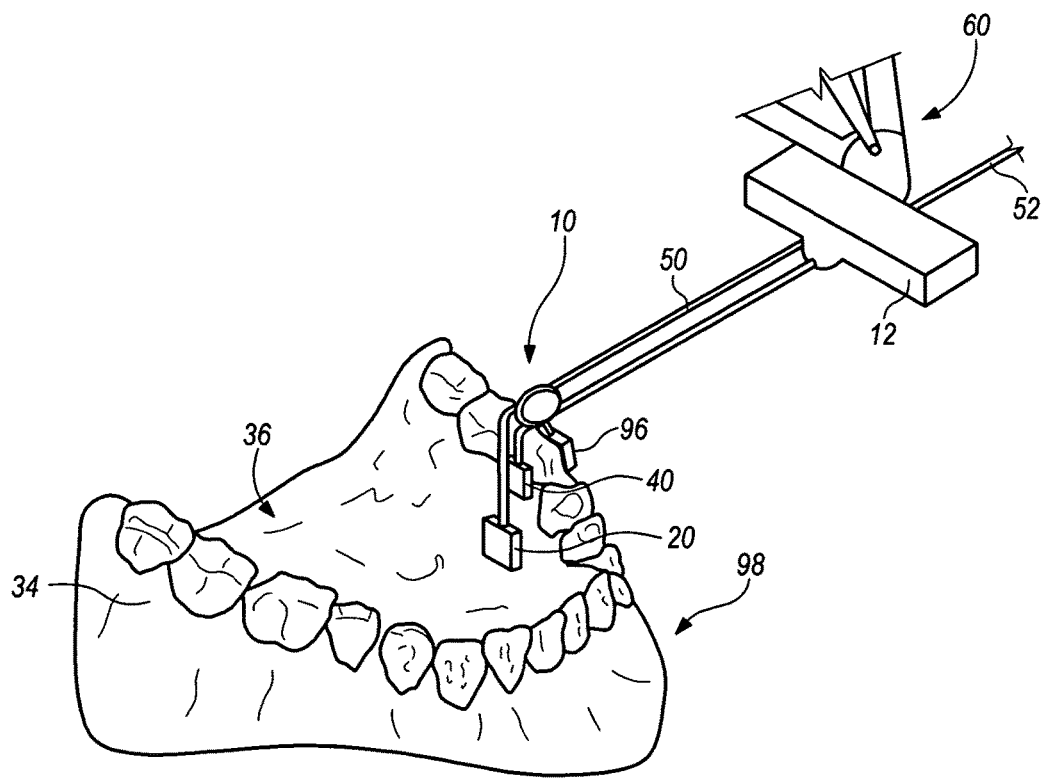
FIG. 5 is a perspective view indicating the apparatus of the present application being to measure tooth mobility on the lower jaw of a patient.

In operation, FIG. 3 schematically represents the placement of device 10 relative to a tooth 86 located along alveolar ridge 34. As may be gleaned from FIG. 3, pads 40 and 42 of second clamp 38 are pressed against tooth 86. Pads 20 and 22 of first clamp 18 firmly pressed against alveolar ridge having an overlying tissue 34. Directional arrows 88 and 90 represent the application of force of pads 20 and 22, as well as pads 40 and 42, of first and second clamps 18 and 38, respectively. Once in this position, the user may engage grip 56 with one hand, steady base member 12 with another hand, and exert a back and forth motion along metering rod 52. Any movement of tooth 86 will then then be detected, via arm 84 and connected gage 60, namely by the movement of indicator element 70 along leg 64 of scale 68. Indicator element 70 will then show the value of the mobility of tooth 86 according to the Miller Scale i.e. 1, 2, or 3 as shown. Of course, indicator element 70 may swing back and forth providing the tooth mobility value on scale 68 in two directions. Again, indicator element 70 may be seen on either side of leg 64 since indicia 66 appear on both sides of leg 64, although only a single side is depicted on FIG. 1. In addition, indicator element 70 may be split into two ends, one end passaging along indicia 66 on leg 64 as shown on FIG. 1 and another end of indicator element 70 passing along similar indicia on leg 64 on the opposite side as that tooth mobility depicted in FIG. 1. Thus, the practitioner is able to read the tooth mobility Miller Scale value using apparatus 10 in the position shown in FIG. 1 or when apparatus 10 is turned upside down from that shown in FIG. 1. Turning to FIGS. 4 and 5, it may be observed that device 10 may be employed to determine mobility of a tooth 92 in an upper jaw 94, FIG. 4, or of a tooth 96 in a lower jaw 98.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A manually operable apparatus for metering a mobility of a tooth positioned in a jaw bone having an alveolar ridge with overlying tissue, comprising:

a base member;

a first clamp, said first clamp being adapted to grip the alveolar ridge having overlying tissue, said first clamp further including a positioning rod connecting to said base member and fixing a distance between said first clamp and said base member;

a second clamp, said second claim comprising a first pad and a second pad, said first pad and said second pad being formed in opposition to one another, said first pad and said second pad being linked to a case, said first and second pads of said second clamp being adapted to grip the tooth for movement therewith, said second clamp further comprising a metering rod, said metering rod being connected to said case linked to said first pad and said second pad, said metering rod extending to and slidingly engaging said base member for back and forth movement of said metering rod, said second clamp and the tooth gripped thereby in two directions, relative to the alveolar ridge, said metering rod further comprising an end portion for manual engagement apart from said base member; and a gauge, said gauge comprising a scale fixed to said base member, a rotatable indicator element rotatably mounted to said scale by a pivot pin extending from said scale, and arm connected to said metering rod and to said rotatable indicator element, to permit back and forth rotational movement of said rotatable indicator element relative to said scale, upon said back and forth movement of said metering rod.

2. The manually operable apparatus of claim 1 in which said first clamp comprises a spring loaded clamp.

3. The manually operable apparatus of claim 1 in which said second clamp comprises a spring loaded clamp.

4. The manually operable apparatus of claim 1 which further comprises a guide for said metering rod, said guide being fastened to said base member to facilitate said sliding engagement and back and forth movement of said metering rod relative to said base member.

5. The manually operable apparatus of claim 1 which further comprises a strain gauge connected to said metering rod for measuring force applied to said metering rod.

6. The manually operable apparatus of claim 1 in which said scale comprises an open frame having a leg, said leg having first and second sides, each of said first and second sides being marked with insignia alignable with said indicator element.

* * * * *